US009962242B2

(12) United States Patent
McDonald et al.

(10) Patent No.: US 9,962,242 B2
(45) Date of Patent: May 8, 2018

(54) REUSABLE DUAL-ARCH ANTERIOR DENTAL IMPRESSION TRAY

(71) Applicant: DENTSPLY SIRONA Inc., York, PA (US)

(72) Inventors: Simon P. McDonald, Katikati (NZ); Alejandro Aubone, Katikati (NZ)

(73) Assignee: DENTSPLY SIRONA Inc., York, PA (US)

(*) Notice: Subject to any disclaimer, the term of this patent is extended or adjusted under 35 U.S.C. 154(b) by 0 days. days.

(21) Appl. No.: 14/420,621

(22) PCT Filed: Aug. 16, 2013

(86) PCT No.: PCT/US2013/055443
§ 371 (c)(1),
(2) Date: Feb. 9, 2015

(87) PCT Pub. No.: WO2014/028889
PCT Pub. Date: Feb. 20, 2014

(65) Prior Publication Data
US 2015/0216633 A1    Aug. 6, 2015

(30) Foreign Application Priority Data

Aug. 16, 2012  (NZ) .................................... 601887
Aug. 8, 2013   (NZ) .................................... 614069

(51) Int. Cl.
*A61C 9/00*  (2006.01)
(52) U.S. Cl.
CPC .................................. *A61C 9/0006* (2013.01)
(58) Field of Classification Search
CPC .................................................. A61C 9/0006
(Continued)

(56) References Cited

U.S. PATENT DOCUMENTS 211,438 A  *  1/1879  Toomey ............... A61C 9/0006
                                                      433/37
2,533,855 A  *  12/1950  Ushanoff ............ A61C 9/0006
                                                      433/37
(Continued)

FOREIGN PATENT DOCUMENTS

CN      201239215      5/2009
DE      4131145 C1     4/1993
(Continued)

OTHER PUBLICATIONS

European Patent Office, Notification of Transmittal of the International Search Report and Written Opinion, PCT/US2013/055443, dated May 12, 2013.

*Primary Examiner* — Cris L Rodriguez
*Assistant Examiner* — Mirayda A Aponte
(74) *Attorney, Agent, or Firm* — Leana Levin; Douglas J. Hura; David A. Zdurne

(57) ABSTRACT

A dual arch anterior dental impression tray includes a generally opened C-shaped mouthpiece and an insert. The mouthpiece having a left end, a right end, and a back side having a concave surface extending from the left end to the right end, the concave surface including a generally longitudinally extending curved groove, the left end and right end each include a connector. The insert including a front portion having a curved frame, the curved frame includes a left end and a right end, the curved frame fits snugly into the curved groove, the insert includes a mesh material extending from and within an area defined by the curved frame, the curved frame left end and right end each include a connector to connect with a respective mouthpiece connector.

20 Claims, 2 Drawing Sheets

(58) Field of Classification Search
USPC .......................................................... 433/37
See application file for complete search history.

(56) References Cited

U.S. PATENT DOCUMENTS

| | | | |
|---|---|---|---|
| 4,445,854 A * | 5/1984 | Bekey | A61C 9/00 433/37 |
| 5,076,785 A | 12/1991 | Tsai | |
| 5,752,826 A | 5/1998 | Andreiko | |
| 5,820,372 A * | 10/1998 | Jones | A61C 9/0006 433/38 |
| 6,302,690 B1 * | 10/2001 | Brandhorst | A61C 9/0006 433/37 |
| 6,447,292 B1 | 9/2002 | Champagne | |
| D631,550 S | 1/2011 | Massad | |
| D686,327 S | 7/2013 | Marumori et al. | |
| D686,732 S | 7/2013 | Marumori et al. | |
| D686,733 S | 7/2013 | Marumori et al. | |
| 2001/0038998 A1 | 11/2001 | Lindquist | |
| 2003/0138754 A1 * | 7/2003 | DiMarino | A61C 9/0006 433/37 |
| 2009/0298007 A1 * | 12/2009 | Walter | A61C 9/0006 433/38 |
| 2010/0075279 A1 | 3/2010 | Ho | |

FOREIGN PATENT DOCUMENTS

| | | | |
|---|---|---|---|
| DE | 10203755 A1 | 7/2003 | |
| DE | 102010049377 A1 | 4/2012 | |
| EP | 1421915 A1 | 5/2004 | |
| FR | 2551654 A1 | 3/1985 | |
| GB | 2329341 A | 3/1999 | |
| JP | S50-033688 A | 3/1975 | |
| KR | 200430758 Y1 | 11/2006 | |
| KR | 20110029456 A * | 3/2011 | |
| WO | 2001037754 A1 | 5/2001 | |
| WO | WO 03043522 A1 * | 5/2003 | ........... A61C 9/0006 |
| WO | 2005046504 A2 | 5/2005 | |
| WO | WO 2005046504 A2 * | 5/2005 | ........... A61C 9/0006 |
| WO | 2009056108 A2 | 5/2009 | |

* cited by examiner

REUSABLE DUAL-ARCH ANTERIOR DENTAL IMPRESSION TRAY

CROSS-REFERENCE TO RELATED APPLICATIONS

This application is a national phase application of international application no. PCT/US2013/055443, filed Aug. 16, 2013, which claims priority to New Zealand Application No. 601887, filed Aug. 16, 2012, and New Zealand Application No. 614069, filed Aug. 8, 2013, the entire contents of which all three are hereby incorporated by reference.

FIELD OF THE INVENTION

The present invention relates generally to the field of dental apparatus and more specifically to dental apparatus for taking impression of teeth, particularly anterior teeth, to assist in the production of dental prosthetics.

BACKGROUND OF THE INVENTION

Dental impression trays are formed as a solid shape that is anatomically shaped to fit over the patient's teeth. An impression material is then secured in the tray, often with an adhesive, before being placed inside the patient's mouth where they bite down on the impression material until it sets. The tray, with set impression material, is then removed from the patient's mouth and is used as a mould to form a model of the patient's dentition.

Dental impression trays can be single-arch trays, where they take an impression of either the upper or lower arch, or dual-arch trays, where they take an impression of both upper and lower arches simultaneously and a bite registration.

To make perfect impressions, moulds, and dental prostheses, the stability of a dual-arch tray is critical. Current bite trays lack this stability due to their construction material and/or design.

SUMMARY OF THE INVENTION

It is an object of the present invention to provide an anterior dual arch dental impression tray that provides an improved anatomical fit in both the horizontal and vertical plane.

It is a further object of the present invention to provide an anterior dual arch dental impression tray that produces an accurate and undistorted impression.

It is yet a further object of the present invention to provide an anterior dual arch dental impression tray that provides the required stability while taking an impression.

The present invention provides a dual arch anterior dental impression tray including a generally opened C-shaped mouthpiece and an insert. The mouthpiece having a front side, a back side, an upper rim, a lower rim, a left end and a right end, the back side having a concave surface extending from the left end to the right end, the concave surface including a generally longitudinally extending curved groove, the left end and right end each include a connector. The insert including a front portion having a curved frame, the curved frame includes a left end and a right end, the curved frame is adapted to fit snugly into the curved groove, the insert includes a mesh material extending from and within an area defined by the curved frame, the curved frame left end and right end each include a connector, wherein the insert left connector is adapted to connect with the mouthpiece left connector and the insert right connector is adapted to connect with the mouthpiece right connector.

DETAILED DESCRIPTION OF THE INVENTION

Figure 1:
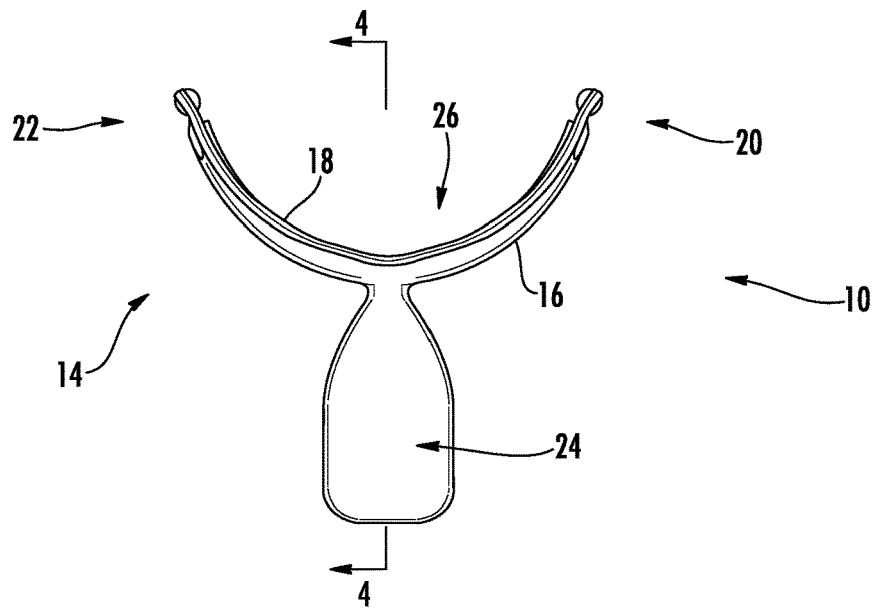
FIG. 1 is a top view of the tray in accordance with one embodiment of the present invention.
Figure 6:
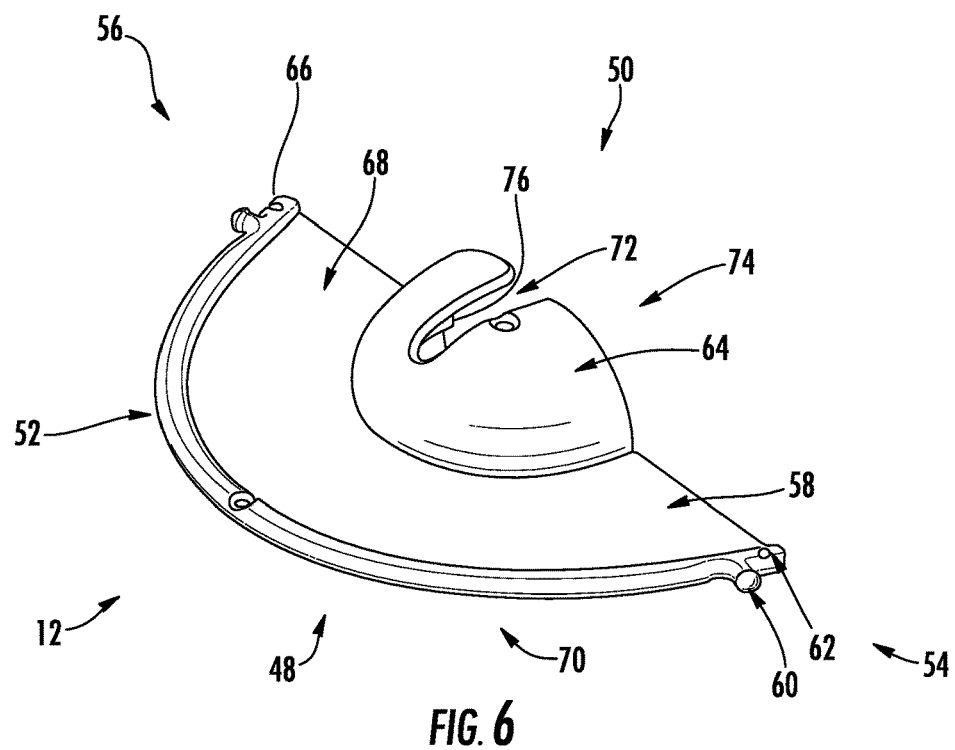
FIG. 6 is a perspective view of an insert in accordance with one embodiment of the present invention, the insert is received by the tray of FIG. 1.

The present invention provides a dual-arch anterior dental impression tray. The dual arch anterior impression tray includes a reusable tray and generally opened C-shaped mouthpiece 10 as shown in FIG. 1 and a single-use insert 12 as shown in FIG. 6.

Figure 2:
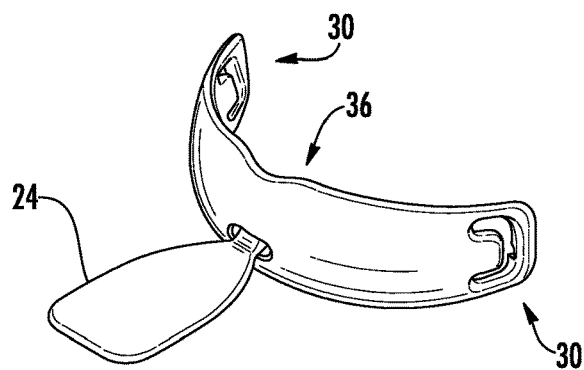
FIG. 2 is a perspective view of the tray of FIG. 1.
Figure 3:
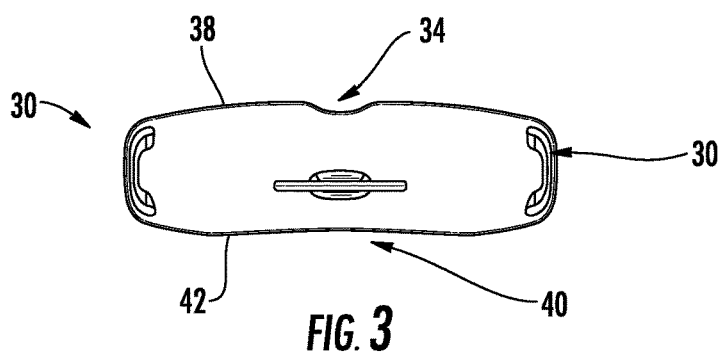
FIG. 3 is a front view of the tray of FIG. 1.
Figure 4:
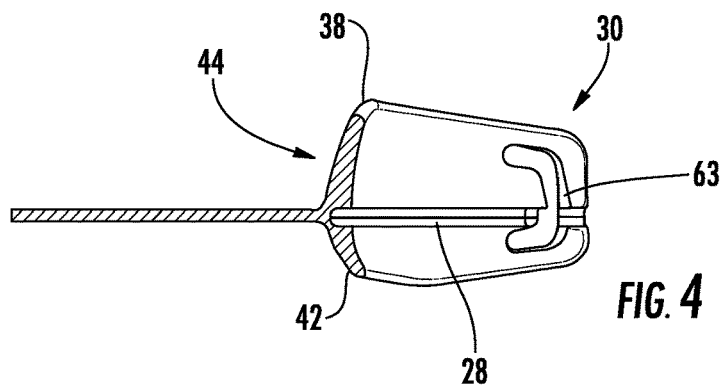
FIG. 4 is a cross-sectional side view of the tray of FIG. 1.
Figure 5:
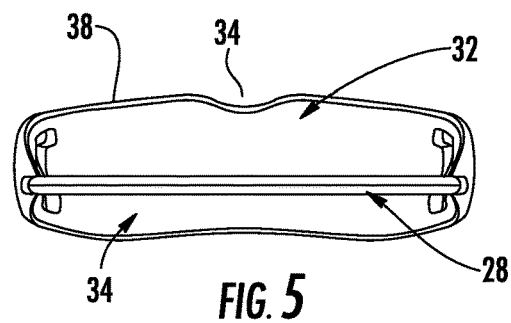
FIG. 5 is a back view of the tray of FIG. 1.

In one embodiment, the mouthpiece 10 is made of solid metal. The mouthpiece 10 includes a main body 14 having a front side 16, back side 18, a left side 20 and a right side 22. A handle 24 extends forward from the front side 16. A concave surface 26 is formed by the back side 18, extending between the left side 20 and the right side 22. A groove 28 runs along the horizontal internal length of the back side 18. The groove 28 ends in a modified horse-shoe shaped cavity 30 on both sides of the tray as shown in FIG. 2. The groove 28 delineates the upper anterior arch 32 and the lower anterior arch 34 of the tray as shown in FIG. 5. The upper anterior arch 32 has a dip 34 at a mid portion 36 of its upper rim 38 that allows for the upper lip frenum, as shown in FIG. 3. The lower anterior arch 34 is slightly concaved 40 at the mid portion 36 of the lower rim 42 to allow for the lower lip frenum, as shown in FIG. 3. The mid portion 36 of tray has vertical concavity 44 extending between the upper rim 38 and the lower rim 42. This vertical concavity 44 has two functions. One function is to avoid the incisors edges of the anterior teeth from touching the tray 10 and creating distortions. The other function of the vertical concavity 44 is to act as a mechanical lock and prevent the vertical movement of the impression material.

In one embodiment, the position of the handle 24 is directly behind the central groove 28. The mouthpiece 10 may be reinforced at the handle 24 as well as along the groove 28. The handle 24 functions as a carrier to place and control the tray 10. Once the patient's lips are closed over the mouthpiece 10, it also allows for self-positioning of the tray while the impression material sets.

In one embodiment, the insert 12 defines a front portion 48 and a back portion 50. The insert 12 includes a curved frame 52, the frame 52 having a left side 54 and a right side 56, a mesh material 58, two notches or connectors 60, 62 at the left side 54 and the right side 56, and lingual bulb 64. The frame 52 of the insert 12 can be completely inserted into the central groove 28 present in the tray 10. The groove 28 of the tray 10 locks the insert 12 in plane of the tray 10. This stabilizes the insert 12 when loading the impression material and also when the patient bites down. The primary notch or generally rearward facing surface 60 on the sides of the insert 12 lock with a forward facing surface 63 of the horse-shoe shaped cavity 30 in the tray 10. The locking of the notch 60 with the cavity 30 prevents the insert 12 from being displaced from the tray 10. It also prevents movement of the impression material when it is loaded and when the patient bites down. The secondary notch 62 stops the insert 12 from moving vertically. The secondary notch 62 may include a raised protrusion 66 on the upper side 68 and lower side 70 at both the left side 54 and right side 56 of the frame 52. The raised protrusions 66 provide an interference fit within the groove 28. In one embodiment, the lingual bulb 64 defines a generally hemispherical shaped portion. The lingual bulb 64 is molded as a single unit on the mesh material 58. Alternatively, it may be molded as two separate symmetrical units that can be put together. When viewed end on, the lingual bulb 64 has a hemispherical shape. The lingual bulb 64 has a split or slit 72 in the middle. The split 72 allows for the lingual frenum. It will be appreciated that the lower portion of the lingual bulb 64 may be identical to the upper portion. Further, the lingual bulb 64 forms an opening 74 which faces away from the front portion 48 of the insert 12. The lingual bulb 64 provides additional locking of the impression material and directs the flow of impression material to accurately copy the internal side of the teeth and soft tissues around. It also aids the flow of impression material such that the resulting impression forms minimal shadows. The lingual bulb 64 also decreases the amount of impression material used when copying the features of the patient's mouth. This makes the central part of the impression five times lighter thereby preventing distortions in bite registration. The lingual bulb 64 provides an area for the patient's tongue while the impression material is setting, without distorting the impression. FIG. 6 also shows a bead 76. The bead 76 may be formed by a seal between sealed halves of the lingual bulb 64. The bead 76 may provide a reinforcement or means to retain the mesh material 58.

The mesh material 58 integrates with the impression material creating an even and thin water proof membrane that separates the upper arch impression from the lower arch impression and in turn constitute the passive bite registration. The surface area of the mesh material 58 included in the insert 12 is greater than the surface area generally required. This additional surface area increases the volume of impression material the insert 12 can hold. The increase in volume of the insert 12 allows for greater accuracy due to passive bite relationship between the upper and lower teeth when they overlap during the bite record; thereby providing an anatomically accurate bite registration.

It will be appreciated that the insert 12 may be designed to be symmetrical, such that the insert 12 need not be oriented with any particular side facing up or down. Such symmetry aids in the ease of assembling the single-use insert 12 with a reusable tray 10.

The device works such that the insert 12 is fitted into the tray 10, making sure that the notches 60, 62 mechanically lock with the horse-shoe cavity 30 in the tray 10. The impression material is loaded in the mesh area of the insert 12 on both sides. The tray 10 is inserted into the patient's mouth by aligning the dip 34 in the upper arch 32 centrally. The patient bites down on the impression material and closes their lips over the tray 10. The patient also holds the handle 24 of the tray 10 using their lips.

Once the impression material is set, the tray 10 is removed from the patient's mouth and sent to the dental laboratory after disinfection. Once the tray is cleaned, it is ready for use with another insert.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

We claim:

1. A dual arch anterior dental impression tray comprising:
   a generally opened C-shaped mouthpiece, the mouthpiece having a front side, a back side, an upper rim, a lower rim, a left end and a right end, the back side having a concave surface extending from the left end to the right end, the concave surface including a generally longitudinally extending curved groove, the left end and right end each include a connector; and
   an insert, the insert including a front portion having a curved frame, the curved frame includes a left end and a right end, the curved frame is adapted to fit snugly into the curved groove, the insert includes a mesh material extending from and within an area defined by the curved frame, the curved frame left end and right end each include a connector, wherein the insert left connector is adapted to connect with the mouthpiece left connector and the insert right connector is adapted to connect with the mouthpiece right connector, wherein the insert includes a back portion with a hemispherical shaped lingual bulb located at a mid portion of the back portion, the lingual bulb defining an opening which faces away from the front portion of the insert, the insert defining a top side and a bottom side and
   wherein the connectors of the mouthpiece include a cut out at the mouthpiece first end and second end, each cut out defining a forward facing surface, and the connectors of the insert include a generally rearward facing notch at the insert first end and a generally rearward facing notch at the second end, wherein each notch is adapted to engage with a respective forward facing surface formed by the respective cut out and
   wherein said connectors of the insert further include a raised protrusion, the raised protrusion providing an interference fit with the groove, and the raised protrusion being separate from said notches.

2. The dual arch anterior dental impression tray of claim 1, wherein the mouthpiece includes a mid portion between the mouthpiece left side and right side, the back side of the mouthpiece at the mid portion forms a concave shape extending between the lower rim and upper rim.

3. The dual arch anterior dental impression tray of claim 1, wherein the lingual bulb includes a slit extending along the top side from the opening and towards the front portion of the insert.

4. The dual arch anterior dental impression tray of claim 3, wherein the lingual bulb includes a slit extending along the bottom side from the opening and towards the front portion of the insert, and the insert is symmetrical.

5. The dual arch anterior dental impression tray of claim 3, wherein the lingual bulb is a single piece component made of plastic material, and the mesh material extends between the frame and the lingual bulb.

6. The dual arch anterior dental impression tray of claim 3, wherein the lingual bulb is formed from a two halves, each half made of plastic material, and the mesh material extends between the frame and the assembled lingual bulb.

7. The dual arch anterior dental impression tray of claim 1, wherein the mouthpiece includes a handle extending from the front side.

8. The dual arch anterior dental impression tray of claim 7, wherein the handle is generally horizontally aligned with the groove, and the cross section of the mouthpiece is reinforced in the area of the handle and groove.

9. The dual arch anterior dental impression tray of claim 1, wherein the mouthpiece is made of a metal material and is intended to be re-used.

10. The dual arch anterior dental impression tray of claim 1, wherein the frame is made of a flexible plastic material and the mesh material is made of nylon material.

11. The dual arch anterior dental impression tray of claim 1, wherein the cut out at the left side extends through the groove and the cut out at the right side extends through the groove.

12. The dual arch anterior dental impression tray of claim 11, wherein each cut out forms a generally horse shoe shaped cavity.

13. The dual arch anterior dental impression tray of claim 1, wherein the insert is symmetrical.

14. The dual arch anterior dental impression tray of claim 1, wherein the groove delineates the mouthpiece into upper and lower anterior arches where the upper arch has a greater height than the lower arch.

15. The dual arch anterior dental impression tray of claim 1, wherein the mouthpiece includes a midportion and includes a dip at the midportion of the upper rim and the lower rim is slightly concave at the mid portion.

16. The dual arch anterior dental impression tray of claim 1, wherein the connectors include horizontal and vertical stabilizers.

17. The dual arch anterior dental impression tray of claim 1, wherein the top side of the insert is symmetrical to the bottom side of the insert.

18. The dual arch anterior dental impression tray of claim 1, wherein the lower portion of the lingual bulb is identical to the upper portion of the lingual bulb.

19. The dual arch anterior dental impression tray of claim 1, wherein the lingual bulb further includes a bead at an area for a patient's tongue, the bead formed by a seal between sealed halves of the lingual bulb, the bead retaining said mesh material.

20. A dual arch anterior dental impression tray comprising:
a generally opened C-shaped mouthpiece, the mouthpiece having a front side, a back side, an upper rim, a lower rim, a left end and a right end, the back side having a concave surface extending from the left end to the right end, the concave surface including a generally longitudinally extending curved groove, the left end and right end each include a connector; and
an insert, the insert including a front portion having a curved frame, the curved frame includes a left end and a right end, the curved frame is adapted to fit snugly into the curved groove, the insert includes a mesh material extending from and within an area defined by the curved frame, the curved frame left end and right end each include a connector, wherein the insert left connector is adapted to connect with the mouthpiece left connector and the insert right connector is adapted to connect with the mouthpiece right connector, wherein the insert includes a back portion with a hemispherical shaped lingual bulb located at a mid portion of the back portion, the lingual bulb defining an opening which faces away from the front portion of the insert, the insert-defining a top side and a bottom side and
wherein the insert left connector and the insert right connector further include a raised protrusion, the raised protrusion providing an interference fit with the groove, and the raised protrusion being separate from said notches.

\* \* \* \* \*